United States Patent
Porter

(10) Patent No.: US 10,179,161 B2
(45) Date of Patent: Jan. 15, 2019

(54) COMPOSITIONS AND METHODS FOR ENHANCING CARDIAC FUNCTION IN THE NEONATE

(71) Applicant: UNIVERSITY OF ROCHESTER, Rochester, NY (US)

(72) Inventor: George Arthur Porter, Pittsford, NY (US)

(73) Assignee: The University of Rochester, Rochester, NY (US)

( * ) Notice: Subject to any disclaimer, the term of this patent is extended or adjusted under 35 U.S.C. 154(b) by 0 days.

(21) Appl. No.: 15/438,700

(22) Filed: Feb. 21, 2017

(65) Prior Publication Data

US 2017/0239322 A1 Aug. 24, 2017

Related U.S. Application Data

(60) Provisional application No. 62/298,133, filed on Feb. 22, 2016.

(51) Int. Cl.
| | |
|---|---|
| *A61K 38/13* | (2006.01) |
| *A61K 9/00* | (2006.01) |
| *C12N 15/113* | (2010.01) |

(52) U.S. Cl.
CPC ............ *A61K 38/13* (2013.01); *A61K 9/0019* (2013.01); *A61K 9/0053* (2013.01); *C12N 15/1137* (2013.01); *C12Y 502/01008* (2013.01); *C12N 2310/11* (2013.01); *C12N 2310/14* (2013.01)

(58) Field of Classification Search
None
See application file for complete search history.

(56) References Cited

PUBLICATIONS

Cooley et al., "Cardiac Transplantation in an 8-Month-Old Female Infant With Subendocardial Fibroelastosis", JAMA, 1986, pp. 1326-1329 (Year: 1986).*
Starnes et al., "Heart, Heart-Lung, and Lung Transplantation in the First Year of Life", Ann Thorac Surg, 1992, pp. 306-310 (Year: 1992).*
Sussman et al., "Prevention of Cardiac Hypertrophy in Mice by Calcineurin Inhibition", Science, 1998, pp. 1690-1693 (Year: 1998).*
"Preclude." Merriam Webster.com Merriam—Webster, n.d. Apr. 26, 2018 p. 1 (Year: 2018).*
Teekakirikul et al., "Cardiac fibrosis in mice with hypertrophic cardiomyopathy is mediated by non-myocyte proliferation and requires Tgf-b", The Journal of Clinical Investigation, 2010; pp. 3520-3529 (Year: 2010).*
Gill et al., "Cyclosporine treatment improves cardiac function and systemic hemodynamics during resuscitation in a newborn piglet model of asphyxia: A dose-response study", Crit Care Med, 2012, pp. 1237-1244 (Year: 2012).*
Dapper et al., "Clinical experience with heart transplantation in infant", European Journal of Cardio-thoracic Surgery, 1998, pp. 1-6 (Year: 1998).*

* cited by examiner

*Primary Examiner* — Lianko G Garyu
(74) *Attorney, Agent, or Firm* — Milstein Zhang & Wu LLC

(57) ABSTRACT

The invention provides novel pharmaceutical compositions and methods for treating newborns in need of enhanced cardiac function, in particular, newborns suffering from cardiomyopathy, or a related disease or condition.

14 Claims, 9 Drawing Sheets
Specification includes a Sequence Listing.

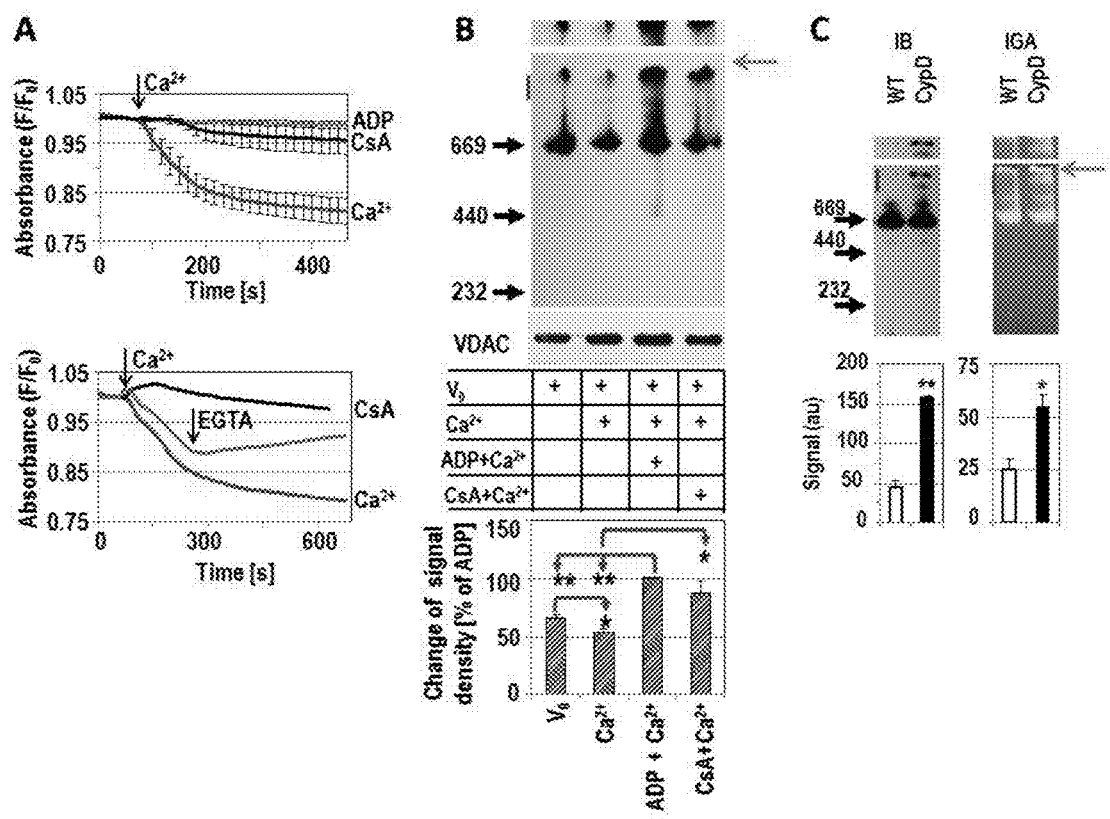
FIG. 1. Supercomplex assembly is regulated by CyPD activity.

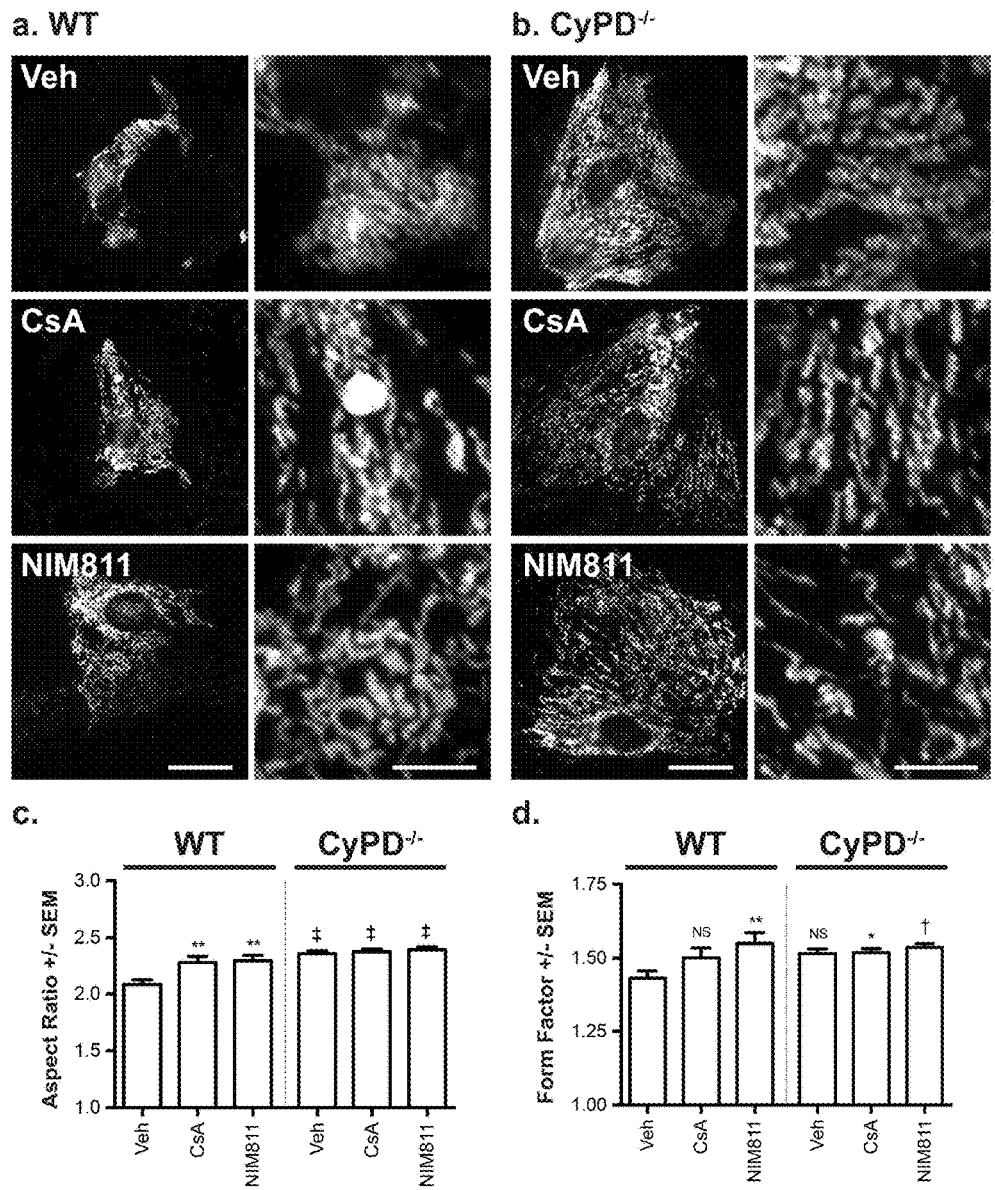
FIG. 2. PTP closure increases mitochondrial maturation.

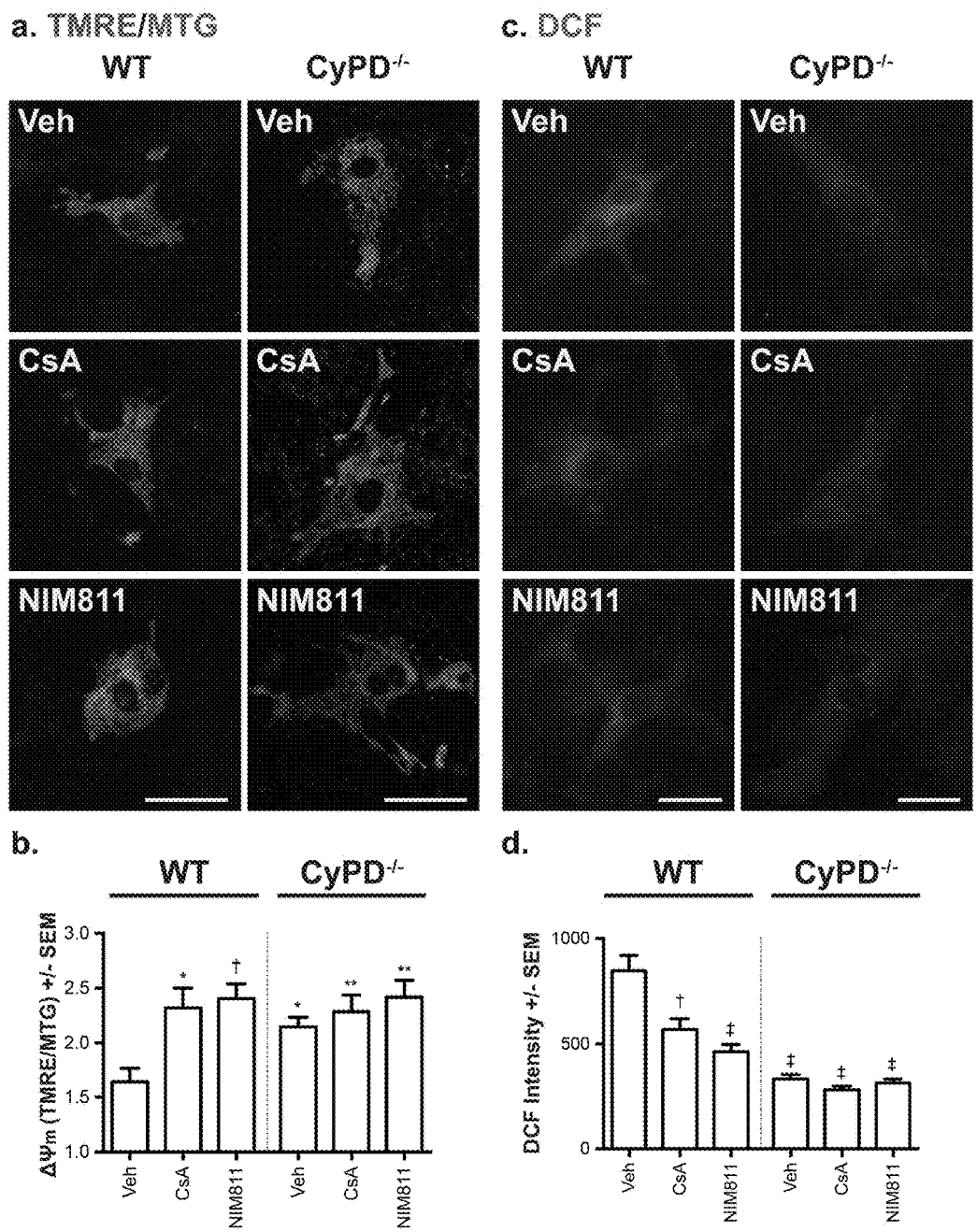
FIG. 3. PTP closure increases mitochondrial function.

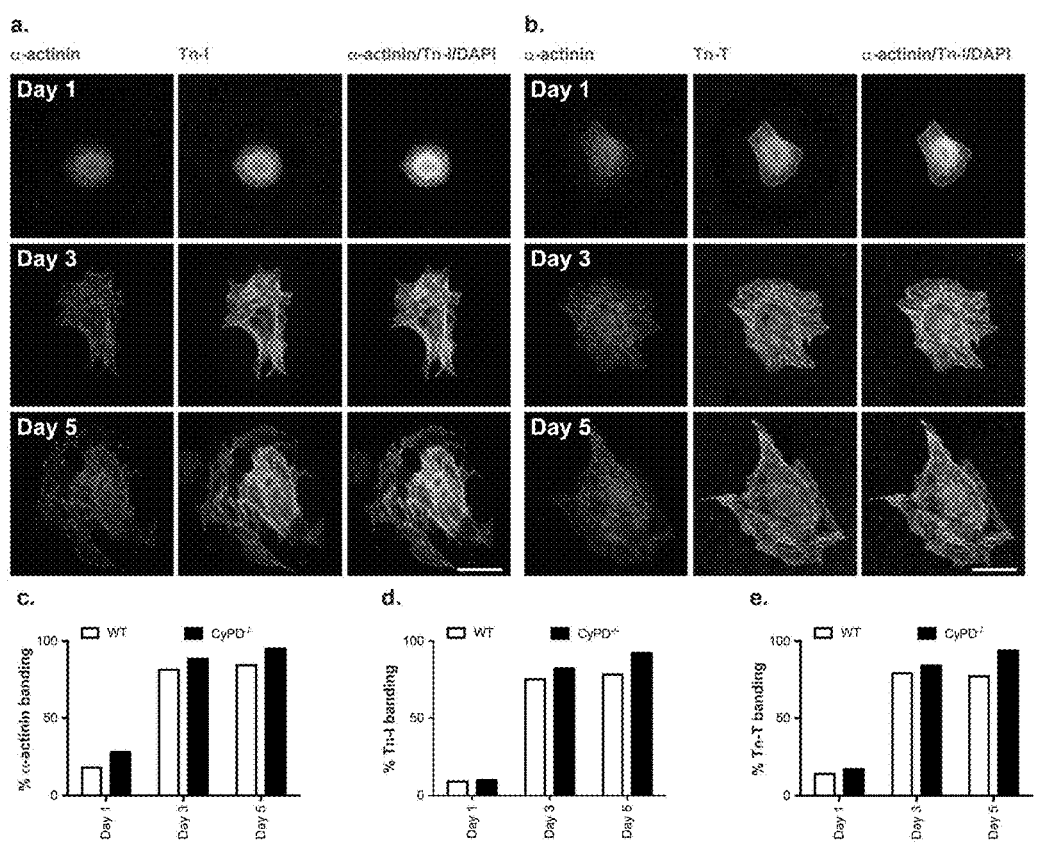
FIG. 4. Method for measuring myocyte differentiation in cultured myocytes *in vitro*.

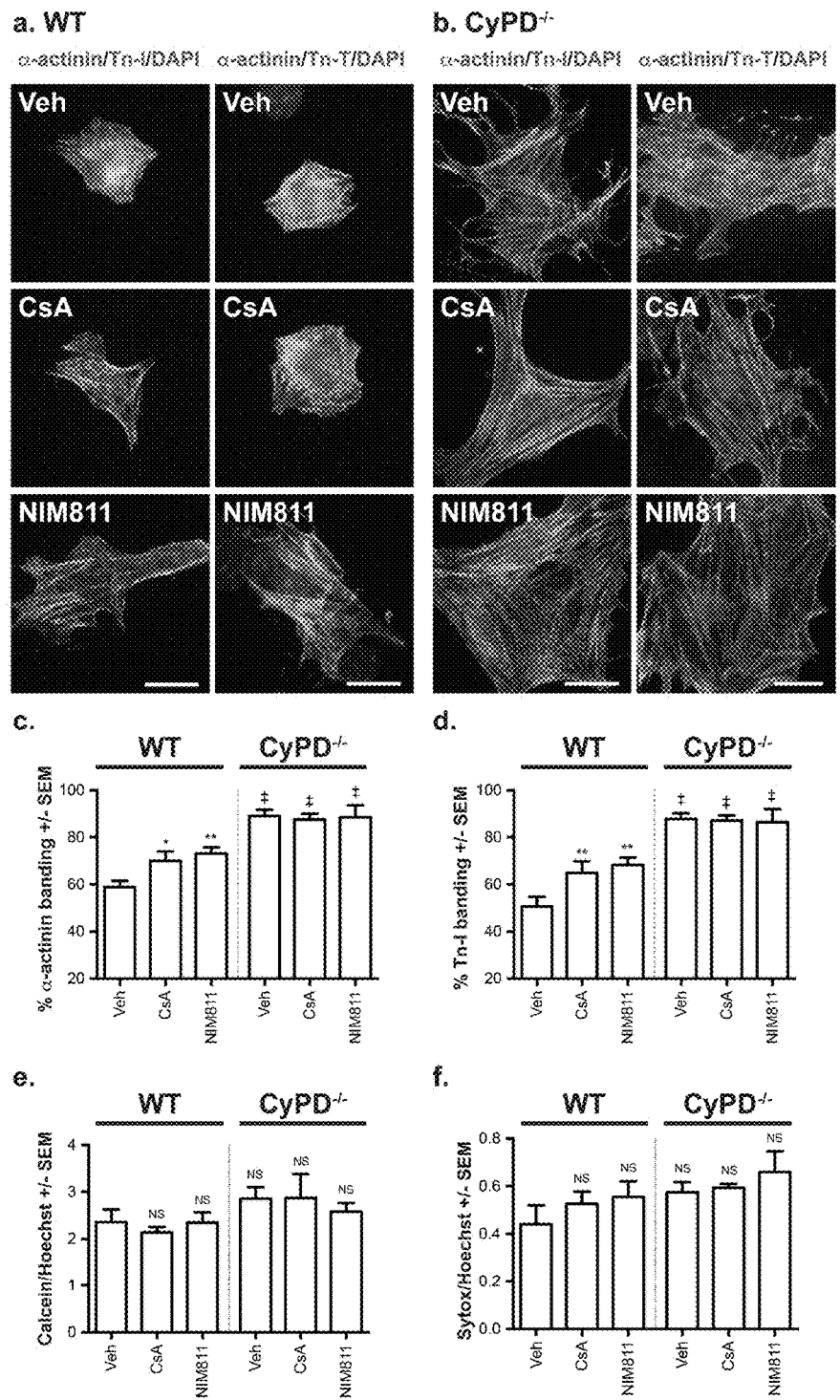
FIG. 5. PTP closure with CsA, NIM811, or CyPD deletion enhances myocyte differentiation.

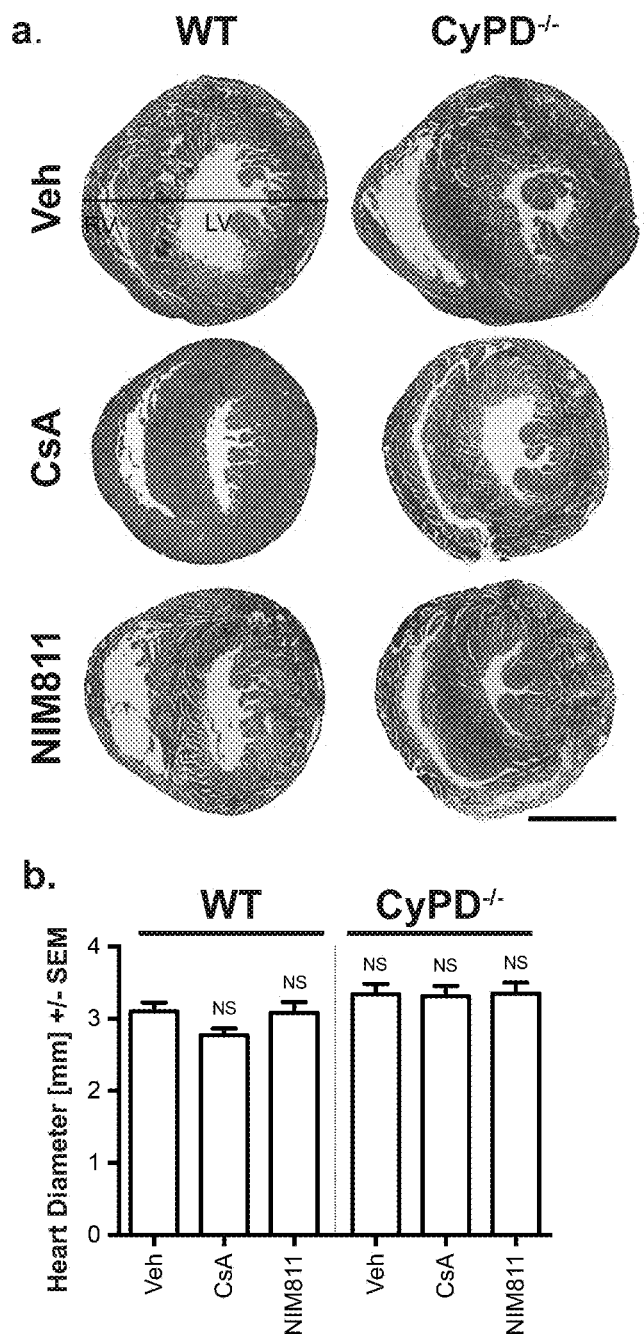
FIG. 6. CyPD inhibition increases LV wall thickness.

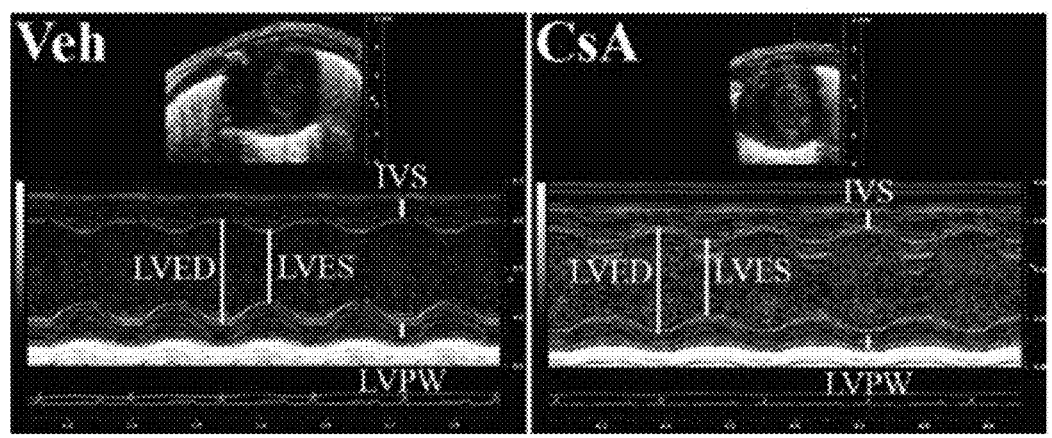
FIG. 7. Neonatal mouse echocardiography.

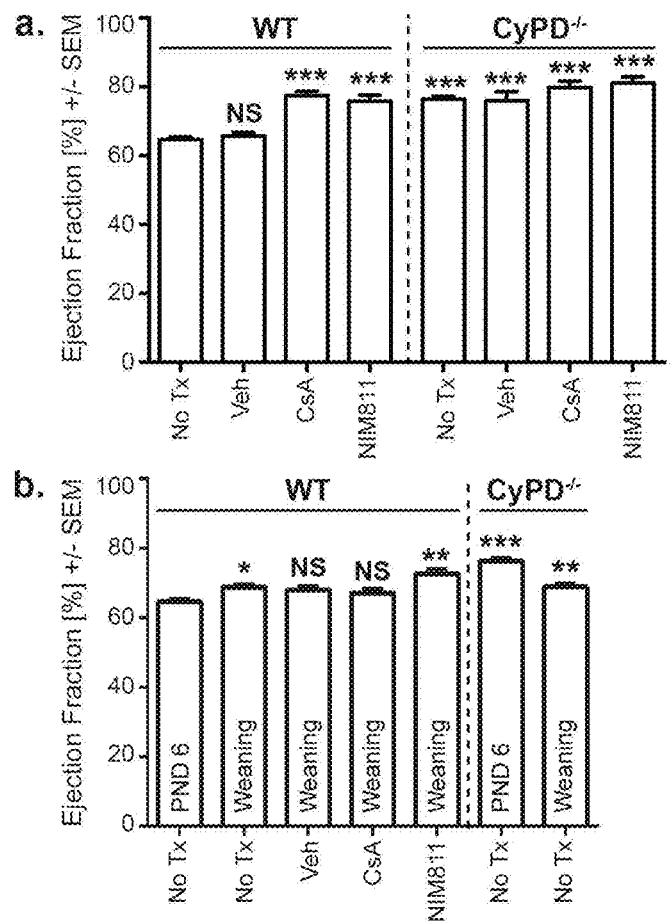
FIG. 8. PTP closure increases neonatal cardiac function.

SEQ. ID NO. 1

MLALRCGSRW LGLLSVPRSV PLRLPAARAC SKGSGDPSSS SSSGNPLVYL DVDANGKPLG
RVVLELKADV VPKTAENFRA LCTGEKGFGY KGSTFHRVIP SFMCQAGDFT NHNGTGGKSI
YGSRFPDENF TLKHVGPGVL SMANAGPNTN GSQFFICTIK TDWLDGKHVV FGHVKEGMDV
VKKIESFGSK SGRTSKKIVI TDCGQLS

SEQ. ID NO. 2

```
gcgggactcg gccttctggg cgcgcgcgac gtcagtttga gttctgtgtt ctccccgccc
gtgtcccgcc cgacccgcgc ccgcgatgct ggcgctgcgc tgcggctccc gctggctcgg
cctgctctcc gtcccgcgct ccgtgccgct gcgcctcccc gcggcccgcg cctgcagcaa
gggctccggc gaccgtcct cttcctcctc ctccgggaac ccgctcgtgt acctggacgt
ggacgccaac gggaagccgc tcggccgcgt ggtgctggag ctgaaggcag atgtcgtccc
aaagacagct gagaacttca gagccctgtg cactggtgag aagggcttcg gctacaaagg
ctccaccttc cacagggtga tcccttcctt catgtgccag gcgggcgact caccaaacca
caatggcaca ggcgggaagt ccatctacgg aagccgcttt cctgacgaga actttacact
gaagcacgtg gggccaggtg tcctgtccat ggctaatgct ggtcctaaca ccaacggctc
ccagttcttc atctgcacca taaagacaga ctggttggat ggcaagcatg ttgtgttcgg
tcacgtcaaa gagggcatgg acgtcgtgaa gaaaatagaa tctttcggct ctaagagtgg
gaggacatcc aagaagattg tcatcacaga ctgtggccag ttgagctaat ctgtggccag
ggtgctggca tggtggcagc tgcaaatgtc catgcaccca ggtggccgcg ttgggctgtc
agccaaggtg cctgaaacga tacgtgtgcc cactccactg tcacagtgtg cctgaggaag
gctgctaggg atgttagacc tcggccagga cccaccacat tgcttcctaa tacccaccct
tcctcacgac ctcatttctg ggcatctttg tggacatgat gtcacccacc ccttgtcaag
cattgcctgt gattgcccag cccagattca tctgtgcctt ggacatggtg atggtgatgg
gttgccatcc aagtgaaagt cttttccttg accaggggg acagtcagtt ttgcaaaagg
actctaatac ctgtttaata ttgtcttcct aattgggata atttaattaa caagattgac
tagaagtgaa actgcaacac taacttcccc gtgctgtggt gtgacctgag ttggtgacac
aggccacaga ccccagagct tggcttttga aacacaactc agggcttttg tgaaggttcc
cccgctgaga tctttcctcc tggttactgt gaagcctgtt ggtttgctgc tgtcgttttt
gaggagggcc catgggggta ggagcagttg aacctgggaa caaacctcac ttgagctgtg
cctagacaat gtgaattcct gtgttgctaa cagaagtggc ctgtaagctc ctgtgctccg
gagggaagca ttcctggta ggctttgatt ttctgtgtg ttaaagaaat tcaatctact
catgatgtgt tatgcataaa acatttctgg aacatggatt tgtgttcacc ttaaatgtga
aaataaatcc tatttctat ggaagactgg tacctggttt ctggaagagg ggtctgtgac
ttggagctga tctttactga gctcgccgtg gcagatgcca tgctcaggac gttcatgtgg
atggtttcat gtcatcgtgc tggcaacttg tcctccctgc cttagagatg aggctcagac
aaacgacctt agcacccata gcctatgcca tgagcactgg ctccaccctg aatcccagct
cctcccctta gtgacccaa gtctgtttcc ctcagctgca taaggaggcg atatagtttg
aatatttgtc cccagccaaa tctcatgttg aactgtaatc cccagtgctg gaggtggggc
ctgctacgag tgtttggat catggggacg ggtatttcat ggcttggtgc tgttttcttg
atggtgaatt attgcaagat acggtcattt aaaattgtgt ggcacctccc cctgccccct
tcttgctcct gctttcacca tgtgacatgc ctgatccccc ttcaccttt gccatggtca
taagcttcct gaggcctccc tggaagctga gcagatgcca gcaccatgct tcctgtacat
cctgcagaac cataagccaa ttaaaccttt taataataa aaaaaaaaa aaa
```

FIG. 9. CyPD Sequences

SEQUENCE LISTING

<160> NUMBER OF SEQ ID NOS: 21

<210> SEQ ID NO 1
<211> LENGTH: 207
<212> TYPE: PRT
<213> ORGANISM: homo sapiens

<400> SEQUENCE: 1

Met Leu Ala Leu Arg Cys Gly Ser Arg Trp Leu Gly Leu Leu Ser Val
1               5                   10                  15

Pro Arg Ser Val Pro Leu Arg Leu Pro Ala Ala Arg Ala Cys Ser Lys
            20                  25                  30

Gly Ser Gly Asp Pro Ser Ser Ser Ser Ser Gly Asn Pro Leu Val
        35                  40                  45

Tyr Leu Asp Val Asp Ala Asn Gly Lys Pro Leu Gly Arg Val Val Leu
    50                  55                  60

Glu Leu Lys Ala Asp Val Val Pro Lys Thr Ala Glu Asn Phe Arg Ala
65                  70                  75                  80

Leu Cys Thr Gly Glu Lys Gly Phe Gly Tyr Lys Gly Ser Thr Phe His
                85                  90                  95

Arg Val Ile Pro Ser Phe Met Cys Gln Ala Gly Asp Phe Thr Asn His
            100                 105                 110

Asn Gly Thr Gly Gly Lys Ser Ile Tyr Gly Ser Arg Phe Pro Asp Glu
        115                 120                 125

Asn Phe Thr Leu Lys His Val Gly Pro Gly Val Leu Ser Met Ala Asn
    130                 135                 140

Ala Gly Pro Asn Thr Asn Gly Ser Gln Phe Phe Ile Cys Thr Ile Lys
145                 150                 155                 160

Thr Asp Trp Leu Asp Gly Lys His Val Val Phe Gly His Val Lys Glu
                165                 170                 175

Gly Met Asp Val Val Lys Lys Ile Glu Ser Phe Gly Ser Lys Ser Gly
            180                 185                 190

Arg Thr Ser Lys Lys Ile Val Ile Thr Asp Cys Gly Gln Leu Ser
        195                 200                 205

<210> SEQ ID NO 2
<211> LENGTH: 2213
<212> TYPE: DNA
<213> ORGANISM: homo sapiens

<400> SEQUENCE: 2
gcgggactcg gccttctggg cgcgcgcgac gtcagtttga gttctgtgtt ctccccgccc      60
gtgtcccgcc cgacccgcgc ccgcgatgct ggcgctgcgc tgcggctccc gctggctcgg     120
cctgctctcc gtcccgcgct ccgtgccgct gcgcctcccc gcggcccgcg cctgcagcaa     180
gggctccggc gacccgtcct cttcctcctc ctccggaaac ccgctcgtgt acctggacgt     240
ggacgccaac gggaagccgc tcggccgcgt ggtgctggag ctgaaggcag atgtcgtccc     300
aaagacagct gagaacttca gagccctgtg cactggtgag aagggcttcg gctacaaagg     360
ctccaccttc cacagggtga tcccttcctt catgtgccag gcgggcgact tcaccaacca     420
caatggcaca ggcgggaagt ccatctacgg aagccgcttt cctgacgaga actttacact     480
gaagcacgtg gggccaggtg tcctgtccat ggctaatgct ggtcctaaca ccaacggctc     540
ccagttcttc atctgcacca taaagacaga ctggttggat ggcaagcatg ttgtgttcgg     600
tcacgtcaaa gagggcatgg acgtcgtgaa gaaaatagaa tctttcggct ctaagagtgg     660

```
gaggacatcc aagaagattg tcatcacaga ctgtggccag ttgagctaat ctgtggccag    720
ggtgctggca tggtggcagc tgcaaatgtc catgcaccca gtggccgcg ttgggctgtc    780
agccaaggtg cctgaaacga tacgtgtgcc cactccactg tcacagtgtg cctgaggaag   840
gctgctaggg atgttagacc tcggccagga cccaccacat tgcttcctaa tacccaccct   900
tcctcacgac ctcatttctg ggcatctttg tggacatgat gtcacccacc ccttgtcaag   960
cattgcctgt gattgcccag cccagattca tctgtgcctt ggacatggtg atggtgatgg  1020
gttgccatcc aagtgaaagt cttttccttg accaaggggg acagtcagtt ttgcaaaagg  1080
actctaatac ctgtttaata ttgtcttcct aattgggata atttaattaa caagattgac  1140
tagaagtgaa actgcaacac taacttcccc gtgctgtggt gtgacctgag ttggtgacac  1200
aggccacaga ccccagagct tggcttttga aacacaactc agggcttttg tgaaggttcc  1260
cccgctgaga tctttcctcc tggttactgt gaagcctgtt ggtttgctgc tgtcgttttt  1320
gaggagggcc catgggggta ggagcagttg aacctgggaa caaacctcac ttgagctgtg  1380
cctagacaat gtgaattcct gtgttgctaa cagaagtggc ctgtaagctc ctgtgctccg  1440
gagggaagca tttcctggta ggctttgatt tttctgtgtg ttaaagaaat tcaatctact  1500
catgatgtgt tatgcataaa acatttctgg aacatggatt tgtgttcacc ttaaatgtga  1560
aaataaatcc tattttctat ggaagactgg tacctggttt ctggaagagg ggtctgtgac  1620
ttggagctga tctttactga gctcgccgtg gcagatgcca tgctcaggac gttcatgtgg  1680
atggtttcat gtcatcgtgc tggcaacttg tcctccctgc cttagagatg aggctcagac  1740
aaacgacctt agcacccata gcctatgcca tgagcactgg ctccaccctg aatcccagct  1800
cctccccttta gtgaccccaa gtctgttcc ctcagctgca taaggaggcg atatagtttg   1860
aatatttgtc cccagccaaa tctcatgttg aactgtaatc cccagtgctg gaggtgggc   1920
ctgctacgag gtgtttggat catggggacg ggtatttcat ggcttggtgc tgttttcttg  1980
atggtgaatt attgcaagat acggtcattt aaaattgtgt ggcacctccc cctgcccct   2040
tcttgctcct gctttcacca tgtgacatgc ctgatccccc ttcaccttttt gccatggtca  2100
taagcttcct gaggcctccc tggaagctga gcagatgcca gcaccatgct tcctgtacat  2160
cctgcagaac cataagccaa ttaaaccttt ttaataataa aaaaaaaaa aaa           2213
```

<210> SEQ ID NO 3
<211> LENGTH: 20
<212> TYPE: PRT
<213> ORGANISM: Unknown
<220> FEATURE:
<223> OTHER INFORMATION: CyPD inhibitor

<400> SEQUENCE: 3

Glu Phe Gly Gly Val Met Cys Val Glu Ser Val Asn Arg Glu Met Ser
1               5                   10                  15
Pro Leu Val Asp
            20

<210> SEQ ID NO 4
<211> LENGTH: 20
<212> TYPE: PRT
<213> ORGANISM: Unknown
<220> FEATURE:
<223> OTHER INFORMATION: CyPD inhibitor

<400> SEQUENCE: 4

Arg Glu Met Ser Pro Leu Val Asp Asn Ile Ala Leu Trp Met Thr Glu

```
1               5                  10                  15
Tyr Leu Asn Arg
            20

<210> SEQ ID NO 5
<211> LENGTH: 20
<212> TYPE: PRT
<213> ORGANISM: Unknown
<220> FEATURE:
<223> OTHER INFORMATION: CyPD inhibitor

<400> SEQUENCE: 5

Met Cys Val Glu Ser Val Asn Arg Glu Met Ser Pro Leu Val Asp Asn
1               5                  10                  15

Ile Ala Leu Trp
            20

<210> SEQ ID NO 6
<211> LENGTH: 20
<212> TYPE: PRT
<213> ORGANISM: Unknown
<220> FEATURE:
<223> OTHER INFORMATION: CyPD inhibitor

<400> SEQUENCE: 6

Leu Leu Ser Leu Ala Leu Val Gly Ala Cys Ile Thr Leu Gly Ala Tyr
1               5                  10                  15

Leu Gly His Lys
            20

<210> SEQ ID NO 7
<211> LENGTH: 20
<212> TYPE: DNA
<213> ORGANISM: Unknown
<220> FEATURE:
<223> OTHER INFORMATION: CyPD inhibitor

<400> SEQUENCE: 7
gtcctcccac tcttagagcc                                              20

<210> SEQ ID NO 8
<211> LENGTH: 20
<212> TYPE: DNA
<213> ORGANISM: Unknown
<220> FEATURE:
<223> OTHER INFORMATION: CyPD inhibitor

<400> SEQUENCE: 8
gtcctcccac tcttagagcc                                              20

<210> SEQ ID NO 9
<211> LENGTH: 20
<212> TYPE: DNA
<213> ORGANISM: Unknown
<220> FEATURE:
<223> OTHER INFORMATION: CyPD inhibitor

<400> SEQUENCE: 9
cttcccgcct gtgccattgt                                              20

<210> SEQ ID NO 10
<211> LENGTH: 20
<212> TYPE: DNA
<213> ORGANISM: Unknown
<220> FEATURE:
```

<223> OTHER INFORMATION: CyPD inhibitor

<400> SEQUENCE: 10
gatgtcctcc cactcttaga                                           20

<210> SEQ ID NO 11
<211> LENGTH: 21
<212> TYPE: DNA
<213> ORGANISM: Unknown
<220> FEATURE:
<223> OTHER INFORMATION: CyPD inhibitor

<400> SEQUENCE: 11
tgtcctccca ctcttagagc c                                         21

<210> SEQ ID NO 12
<211> LENGTH: 25
<212> TYPE: DNA
<213> ORGANISM: Unknown
<220> FEATURE:
<223> OTHER INFORMATION: siRNA

<400> SEQUENCE: 12
ggaggacauc caagaagauu gucat                                     25

<210> SEQ ID NO 13
<211> LENGTH: 27
<212> TYPE: RNA
<213> ORGANISM: Unknown
<220> FEATURE:
<223> OTHER INFORMATION: siRNA

<400> SEQUENCE: 13
augacaaucu ucuuggaugu ccuccca                                   27

<210> SEQ ID NO 14
<211> LENGTH: 25
<212> TYPE: DNA
<213> ORGANISM: Unknown
<220> FEATURE:
<223> OTHER INFORMATION: siRNA

<400> SEQUENCE: 14
cccaaagaca gcugagaacu ucaga                                     25

<210> SEQ ID NO 15
<211> LENGTH: 27
<212> TYPE: RNA
<213> ORGANISM: Unknown
<220> FEATURE:
<223> OTHER INFORMATION: siRNA

<400> SEQUENCE: 15
ucugaaguuc ucagcugucu uugggac                                   27

<210> SEQ ID NO 16
<211> LENGTH: 25
<212> TYPE: DNA
<213> ORGANISM: Unknown
<220> FEATURE:
<223> OTHER INFORMATION: siRNA

<400> SEQUENCE: 16
gcuccaccuu ccacagggug auccc                                     25

```
<210> SEQ ID NO 17
<211> LENGTH: 27
<212> TYPE: RNA
<213> ORGANISM: Unknown
<220> FEATURE:
<223> OTHER INFORMATION: siRNA

<400> SEQUENCE: 17
gggaucaccc uguggaaggu ggagccu                                      27

<210> SEQ ID NO 18
<211> LENGTH: 25
<212> TYPE: DNA
<213> ORGANISM: Unknown
<220> FEATURE:
<223> OTHER INFORMATION: siRNA

<400> SEQUENCE: 18
cagacugguu ggauggcaag caugt                                        25

<210> SEQ ID NO 19
<211> LENGTH: 27
<212> TYPE: RNA
<213> ORGANISM: Unknown
<220> FEATURE:
<223> OTHER INFORMATION: siRNA

<400> SEQUENCE: 19
acaugcuugc cauccaacca gucuguc                                      27

<210> SEQ ID NO 20
<211> LENGTH: 25
<212> TYPE: DNA
<213> ORGANISM: Unknown
<220> FEATURE:
<223> OTHER INFORMATION: siRNA

<400> SEQUENCE: 20
ggcuaaugcu gguccuaaca ccaac                                        25

<210> SEQ ID NO 21
<211> LENGTH: 27
<212> TYPE: RNA
<213> ORGANISM: Unknown
<220> FEATURE:
<223> OTHER INFORMATION: siRNA

<400> SEQUENCE: 21
guugguguua ggaccagcau uagccau                                      27
```

COMPOSITIONS AND METHODS FOR ENHANCING CARDIAC FUNCTION IN THE NEONATE

PRIORITY CLAIMS AND RELATED APPLICATIONS

This application claims the benefit of priority from U.S. Provisional Application No. 62/298,133, filed Feb. 22, 2016, the entire content of which is incorporated herein by reference for all purposes.

TECHNICAL FIELD OF THE INVENTION

The invention generally relates to novel pharmaceutical compositions and therapeutic methods. More particularly, the invention relates to novel pharmaceutical compositions and therapeutic methods for treating newborns in need of enhanced cardiac function, in particular, newborns suffering from cardiomyopathy, or a related disease or condition.

BACKGROUND OF THE INVENTION

Cardiomyopathy refers to diseases where the heart muscle is abnormal. These diseases have many causes, signs and symptoms. The main types of cardiomyopathy include dilated, hypertrophic and restrictive cardiomyopathy. Those with cardiomyopathy are often at risk of dangerous forms of irregular heart rate and sudden cardiac death. Cardiomyopathy can be acquired where a patient develops the condition due to another disease, condition, or factor. Cardiomyopathy can also be inherited due to genetic abnormalities passed from the earlier generation.

Neonatal heart failure remains a significant problem resulting from a wide array of cardiac and non-cardiac causes. In the United States, the incidence of neonatal cardiomyopathy is approximately 0.87/100,000 or 12,000-35,000 U.S. children/year, with up to 70% of these patients present being infants. (Hsu D T, Pearson G D. Heart failure in children: part I: history, etiology, and pathophysiology. Circ Heart Fail 2009; 2:63-70.) Around three thousand surgeries are performed each year on infants in the first month of life to address a potentially fatal condition.

Cardiomyopathies in newborns are the result of energetic and functional deficiencies of the myocyte, including mitochondrial disease, genetic defects sometimes associated with congenital heart disease (CHD), and myocardial stunning after cardiac surgery for CHD.

Therapy for cardiomyopathies is typically non-specific because the etiology is often difficult to define in a timely manner. Patients are treated with inotropic agents and sometimes "mitochondrial" reagents such as carnitine and coenzyme Q that do not treat the primary cellular defect.

Despite persistent efforts over the past decades, understanding and management of cardiomyopathies in newborns remain challenging. There is an ongoing and urgent need for novel and improved therapeutics and methods.

SUMMARY OF THE INVENTION

The invention is based in part on the unexpected discovery of novel pharmaceutical compositions and therapeutic methods for treating newborns in need of enhanced cardiac function, for examples, newborns suffering from cardiomyopathy, or a related disease or condition.

In one aspect, the invention generally relates to a method for treating a neonate of a mammal, including a human, to enhance its cardiac function. The method includes administering to a subject in need thereof an inhibitor of Cyclophilin D (CyPD), or a pharmaceutically acceptable form thereof, in an amount effective to cause enhancement of the cardiac function of the subject.

In another aspect, the invention generally relates to a method for preventing or reducing the risk of cardiomyopathy in a neonate of a mammal, including a human. The method includes administering to a subject at risk for cardiomyopathy an inhibitor of CyPD, or a pharmaceutically acceptable form thereof, in an amount effective to cause enhancement of the cardiac function of the subject thereby preventing or reducing the risk of cardiomyopathy, decreased cardiac function, or decreased cardiac output, or a related disease or condition.

In yet another aspect, the invention generally relates to a pharmaceutical composition comprising an inhibitor of CyPD or a pharmaceutically acceptable form thereof, in an amount effective in enhancing cardiac function, or preventing or treating cardiomyopathy, decreased cardiac function, or decreased cardiac output, or a related disease or condition thereof, in a neonate of a mammal, including a human, and a pharmaceutically acceptable carrier.

In yet another aspect, the invention generally relates to a unit dosage form comprising a pharmaceutical composition disclosed herein. In certain embodiments, the unit dosage is in the form of a tablet or capsule suitable for oral administration. In certain embodiments, the unit dosage is in the form of a liquid solution or suspension suitable for intravenous, intramuscular, or subcutaneous administration.

BRIEF DESCRIPTION OF THE DRAWINGS

FIG. 1 depicts exemplary data showing that supercomplex assembly is regulated by CyPD activity.

FIG. 2 depicts exemplary data showing that CyPD null myocytes are more differentiated than WT (wild type) myocytes in vitro.

FIG. 3 depicts exemplary data showing that CyPD inhibition increases LV wall thickness.

FIG. 4 depicts exemplary data on neonatal mouse echocardiography.

FIG. 5 depicts exemplary data showing that PTP closure increases mitochondrial maturation.

FIG. 6 depicts exemplary data showing that PTP closure increases mitochondrial membrane potential.

FIG. 7 depicts exemplary data showing that PTP closure enhances myocyte differentiation.

FIG. 8 depicts exemplary data showing that PTP closure increases neonatal cardiac function.

FIG. 9 depicts CyPD Sequences.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Cyclophilin D (CyPD) is a member of the peptidyl-prolyl cis-trans isomerase (PPlase) family. This protein is part of the mitochondrial permeability transition pore in the inner mitochondrial membrane. Although the methods described herein are not limited to humans, GenBank Accession No. NP 005720.1 (SEQ ID NO: 1) provides a protein sequence for human cyclophilin D that is encoded by the nucleotide sequence set forth under GenBank Accession No. NM 005729.3 (SEQ ID NO: 2). Amino acids 1-29 of SEQ ID NO: 1 encode a signal peptide. The mature peptide is encoded by amino acids 30-207 of SEQ ID NO: 1. The information, including the sequences, provided under GenBank Accession No. NP 005720.1 and GenBank Accession No. NM 005729.3, is herein incorporated in its entirety by this reference.

The CyPD sequences contemplated herein include full-length wild-type sequences, as well as allelic variants or homologs that retain at least one CyPD activity, for example, PPlase activity. For example, the sequences set forth herein can comprise one or more amino acid substitutions. CyPD sequences from other species are also available to those of skill in the art. CyPD sequences also include sequences that are at least 50%, 60%, 70%>, 80%, 90%, 95%, 98%, 99% or 100% identical to a CyPD sequence set forth herein that still retains at least one activity of CyPD, for example, PPlase activity.

Those of skill in the art readily understand how to determine the identity of two polypeptides or nucleic acids. For example, the identity can be calculated after aligning the two sequences so that the identity is at its highest level.

Another way of calculating identity can be performed by published algorithms. Optimal alignment of sequences for comparison can be conducted using the algorithm of Smith and Waterman 1981 *Adv. Appl. Math.* 2: 482, by the alignment algorithm of Needleman and Wunsch, 1970 *J Mol. Biol.* 48: 443, by the search for similarity method of Pearson and Lipman, 1988 *Proc. Natl. Acad. Sci. U.S.A.* 85: 2444, by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden 1999 *FEMS Microbiol. Lett.* 174: 247-250 available from the National Center for Biotechnology Information (http://www.ncbi.nlm.nih.gov/blast/b12seq/b12.html), or by inspection.

The same types of identity can be obtained for nucleic acids by, for example, the algorithms disclosed in Zuker 1989 *Science* 244:48-52; Jaeger, et al. 1989 *Proc. Natl. Acad. Sci. USA* 86:7706-7710; Jaeger, et al. 1989 *Methods Enzymol.* 183:281-306, that are herein incorporated by this reference for at least material related to nucleic acid alignment. It is understood that any of the methods typically can be used and that, in certain instances, the results of these various methods may differ, but the skilled artisan understands if identity is found with at least one of these methods, the sequences would be said to have the stated identity.

For example, as used herein, a sequence recited as having a particular percent identity to another sequence refers to sequences that have the recited identity as calculated by any one or more of the calculation methods described above. For example, a first sequence has 80 percent identity, as defined herein, to a second sequence if the first sequence is calculated to have 80 percent identity to the second sequence using the Zuker calculation method even if the first sequence does not have 80 percent identity to the second sequence as calculated by any of the other calculation methods. As yet another example, a first sequence has 80 percent identity, as defined herein, to a second sequence if the first sequence is calculated to have 80 percent identity to the second sequence using each of the calculation methods (although, in practice, the different calculation methods will often result in different calculated identity percentages).

As used herein, the term "effective amount" of an active agent refers to an amount sufficient to elicit the desired biological response. Such effective amounts are readily ascertained by one of ordinary skill in the art and are based on various factors. As will be appreciated by those of ordinary skill in this art, the effective amount of a compound of the invention may vary depending on such factors as the desired biological endpoint, the pharmacokinetics of the compound, the disease being treated, the mode of administration, and the patient. In some embodiments, the effective amount is the amount that provides relief to cardiomyopathy or enhances cardiac function of a neonate mammal.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the terms "prevent", "preventing", or "prevention" refer to a method for precluding, delaying, averting, or stopping the onset, incidence, severity, or recurrence of a disease or condition. For example, a method is considered to be a prevention if there is a reduction or delay in onset, incidence, severity, or recurrence of a disease or condition or one or more symptoms thereof in a subject susceptible to the disease or condition as compared to a subject not receiving the method. The disclosed method is also considered to be a prevention if there is a reduction or delay in onset, incidence, severity, or recurrence of osteoporosis or one or more symptoms of a disease or condition in a subject susceptible to the disease or condition after receiving the method as compared to the subject's progression prior to receiving treatment. Thus, the reduction or delay in onset, incidence, severity, or recurrence of osteoporosis can be about a 5, 10, 20, 30, 40, 50, 60, 70, 80, 90, 100%, or any amount of reduction in between.

As used herein, a "pharmaceutically acceptable form" of a disclosed compound includes, but is not limited to, pharmaceutically acceptable salts, esters, hydrates, solvates, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In some embodiments, a "pharmaceutically acceptable form" includes, but is not limited to, pharmaceutically acceptable isomers and stereoisomers, prodrugs and isotopically labeled derivatives thereof.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical acceptable forms (e.g., salts, esters, and prodrugs) thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. (See, WO 2007/005643, WO 2007/005644, WO 2007/016361, and WO 2007/016431.)

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

DETAILED DESCRIPTION OF THE INVENTION

The invention provides novel pharmaceutical compositions and methods for treating newborns in need of enhanced cardiac function, for examples newborns suffering from cardiomyopathy, or a related disease or condition.

In a patient with cardiomyopathy, the heart muscle becomes enlarged, thickened, or and/or stiffened such that the heart can no longer contract or relax normally. Cardiomyopathies are either confined to the heart or are part of a generalized disorder, which can lead to death or progressive heart failure. As cardiomyopathy worsens, the heart becomes less able to pump blood through the body and maintain a normal electrical rhythm, which can lead to heart failure or arrhythmias. The weakening of the heart also can cause other complications, such as heart valve problems. Heart failure can cause fluid to build up in the lungs, ankles, feet, legs, or abdomen.

The neonatal period is a time of transition between the bioenergetically immature myocardium of the embryo/fetus and the mature myocardium of the adult heart. In this developmental window, the neonatal heart is more "fetal" than "mature." The neonatal heart is highly proliferative and can regenerate, but it loses this capacity by seven days of age in the mouse. Furthermore, the pathways that regulate this transition are intimately related to mitochondrial biology and oxidative stress pathways play a critical role in this process. (Porrello, et al. 2011 *Science* 331: 1078-1080; Puente, et al. 2014 *Cell* 157: 565-579; Argaud, et al. 2008 *Am J Physiol Heart Circ Physiol* 294: H386-391.)

It has been shown that mitochondrial function regulates cardiac development. As the embryonic heart develops, mitochondria attain a more mature structure as the electron transport chain (ETC) assembles and activates. The changes are due to closure of the mitochondrial permeability transition pore (PTP), and the subsequent fall in mitochondrial-derived oxidative stress promotes further myocyte differentiation. Studies have also revealed that the PTP is derived from unassembled ATP synthase molecules. Evidence disclosed herein indicates that these changes are linked by the activity of the chaperone protein, Cyclophilin D (CyPD) and that CyPD inhibition increases mitochondrial maturation, myocyte differentiation and cardiac function.

CyPD, located in the matrix of mitochondria, is only a modulatory, but not structural component of the mitochondrial permeability transition pore. The pore opening raises the permeability of the mitochondrial inner membrane, allows influx of cytosolic molecules into the mitochondrial matrix, increases the matrix volume, and disrupts the mitochondrial outer membrane. As a result, the mitochondria fall into a functional disorder, so the opening of the pore plays an important role in cell death.

The present invention undertakes a unique approach to impact the neonatal heart function by targeting the mitochondrial pathways. A key feature of the invention is that the unique therapeutic approach disclosed herein is aimed at causing pharmacologic closure of the PTP leading to enhanced or increased cardiac function in the early neonatal heart. This is possible during this specific window of time because the myocytes of the heart are relatively immature during the first week of life, and closing the PTP enhances their differentiation, leading to increased cardiac contractility and cardiac output. Pharmaceutical compositions disclosed herein inhibit the protein CyPD to close the PTP. The therapy approach disclosed herein can be used to treat neonates with cardiomyopathies caused by genetic mutations, environmental factors, and therapies/surgeries for congenital heart defects.

Another unique feature of the invention is the repurposing of clinically available drugs (e.g., NIM811, Debio025, cyclosporine A) that inhibit CyPD, allowing such clinically available drugs to be quickly available to treating newborns with cardiomyopathy, or related diseases or conditions.

In vitro studies of various agents have been reported, for example, Alisporivir (a.k.a., Debio025) and NIM811 (N-methyl-4-isoleucine-cyclosporin) and Sangliferin A. (Hopkins, et al. 2012 *Viruses* 4, 2558-2577; Clarke, et al. 2002 *J Biol Chem* 277, 34793-34799). The affinity of CsA and NIM811 for CyPD is similar. Both fully protect against PTP opening at 1 µM, although CsA becomes less effective at higher doses possibly due to inhibition of the calcineurin pathway. These reagents have higher affinity for CyPD than for CyPA: For example, CsA has a $K_i$ for cardiac mitochondrial swelling of 13.7 nM and for inhibition of CyPD's enzymatic activity of 3.8 nM, and NIM811 was found to be as potent as CsA to prevent PTP opening. (Waldmeier, et al. 2002 *Mol Pharmacol* 62, 22-29; Griffiths, et al. 1991 *Biochem J* 274 (Pt 2), 611-614.) As a CyPD inhibitor, Alisporivir is about as potent as CsA, while Sangliferin A is more potent ($K_{0.5}$=2 nM). (Gomez, et al. 2007 *Am J Physiol Heart Circ Physiol* 293, H1654-1661; Clarke, et al. 2002 *J Biol Chem* 277, 34793-34799.)

In studies of reperfusion injury in the mature heart using single dosing strategies, CsA was used at various doses: 5 mg/Kg IV, 10 mg/kg IV. It protected the brain during hypoglycemic coma at a dose of 50 mg/Kg IV. (Cour, et al. 2011 *Eur Heart J* 32, 226-235; Argaud, et al. 2005 *J Mol Cell Cardiol* 38, 367-374; Friberg, et al. 1998 *J Neurosci* 18, 5151-5159.) NIM811 has been shown to inhibit the PTP and protect adult animals against reperfusion injury at single doses of 2.5 mg/Kg, 5 mg/Kg IV, and 10 mg/Kg IV. (Cour, et al. 2011 *Eur Heart J* 32, 226-235; Argaud, et al. 2005 *J Mol Cell Cardiol* 38, 367-374; Argaud, et al. 2005 *Circulation* 111, 194-197; Chen, et al. 2012 *Molecular Biology Reports* 39, 6049-6057.)

Alisporivir has also studied in vivo to treat various forms of muscular dystrophy at 10-100 mg/Kg/d PO, IV, and IP and NSAID-induced intestinal ulcerations at 10 mg/Kg. (Millay, et al. 2008 *Nat Med* 14, 442-447; Reutenauer, et al. 2008 *Br J Pharmacol* 155, 574-584; Tiepolo, et al. 2009 *Br J Pharmacol* 157, 1045-1052; Wissing, et al. 2010 *Neuromuscul Disord* 20, 753-760; LoGuidice, et al. 2010 *Toxicol. Sci* 118, 276-285.) In the heart, Alisporivir has been used to ameliorate the effects of ischemia reperfusion injury at 10 mg/Kg IV, but it has not been used in the developing heart and the earliest exposure in the literature is in three-week old mice, to the best of our knowledge. (Gomez, et al. 2007 *Am J Physiol Heart Circ Physiol* 293, H1654-1661; Reutenauer, et al. 2008 *Br J Pharmacol* 155, 574-584.)

Human studies have also been reported in connection with some of these agents. CsA has recently been tested to prevent reperfusion injury during acute myocardial infarction by inhibiting CyPD and closing the PTP. (Mewton, et al. 2010 *J Am Coll Cardiol* 55, 1200-1205; Piot, et al. 2008 *N Engl J Med* 359, 473-481; Cung, et al. 2015 *N Engl J Med* 373, 1021-1031.) In a Phase I-II trial, NIM811 was given in to adult patients a 14-day trial in doses of 10-600 mg twice a day for the treatment of Hepatitis C used doses of 25 mg to 1,200 mg (daily oral dose).

In one aspect, the invention generally relates to a method for enhancing cardiac function of a neonate of a mammal, including a human. The method includes administering to a subject in need thereof an inhibitor of CyPD, or a pharmaceutically acceptable form thereof, in an amount effective to cause enhancement of the cardiac function of the subject.

In another aspect, the invention generally relates to a method for preventing or reducing the risk of or treating cardiomyopathy in a neonate of a mammal, including a human. The method includes administering to a subject at risk for cardiomyopathy an inhibitor of CyPD, or a pharmaceutically acceptable form thereof, in an amount effective to cause enhancement of the cardiac function of the subject thereby preventing or reducing the risk of or treating cardiomyopathy, decreased cardiac function, or decreased cardiac output, or a related disease or condition.

Methods may be employed in connection with any disease or condition where an enhanced cardiac function is deemed beneficial to the neonate, whether to treat, prevent or minimize the impact of such a disease or condition. In certain embodiments of the method, the neonate suffers from cardiomyopathy, decreased cardiac function or decreased cardiac output. In certain embodiments of the method, the neonate is at risk for cardiomyopathy, decreased cardiac function, or decreased cardiac output.

Methods of the invention may be employed to treat a neonate of any suitable age, for example, aged 1 day to about 8 weeks (e.g., from about 1 day to 6 weeks, from about 1 day to about 2 weeks). In certain embodiments, the neonate being treated is aged 1 day to about 14 days (e.g., 1, 2, 3, 4, 5, 6, 7, 8, 9, 10, 11, 12, 13 or 14 days of age; from about 1 day to about 10 days, from about 1 day to about 7 days, from about 1 day to about 3 days). For examples, potential patients include newborns in the first week of life undergoing open-heart surgery to repair or palliate complex congenital heart defects who have a primary cardiomyopathy from their heart disease or a secondary cardiomyopathy from the effects of open heart surgery. Potential patients include newborns with primary cardiomyopathies from genetic mutations in genes encoding mitochondrial proteins or proteins involved in cardiac development or function.

Any suitable CyPD inhibitors may be applied to the method of the invention. An inhibitor of CyPD can be a small molecule, a large molecule, a polymer, a peptide or a nucleic acid molecule now known or identified in the future that inhibits at least one function of CyPD. Inhibitors or CyPD may be an organic compound or an inorganic compound. Therapeutically active derivatives and pharmaceutically acceptable forms (e.g., salts, esters or pro-drugs) of all of the compounds set forth herein are also contemplated.

In certain embodiments, the inhibitor of CyPD is selected from Cyclosporine A (CsA), N-methyl-4-isoleucine cyclosporine, Alisporivir, GW5 and Sanglifehrin A.

In certain embodiments of the method, the inhibitor of CyPD is immunosuppressive (e.g., CsA). It is noted that for certain patients and/or diseases or conditions being treated, immunosuppressive agents may be preferably avoided. In certain preferred embodiment, the CyPD inhibitor is non-immunosuppressive (e.g., N-methyl-4-isoleucine cyclosporine, Alisporivir, GW5 and Sanglifehrin A).

Other CyPD inhibitors include peptides such as, for example,
EFGGVMCVESVNREMSPLVD (SEQ ID NO: 3),
REMSPLVDNIALWMTEYLNR (SEQ ID NO: 4),
MCVESVNREMSPLVDNIALW (SEQ ID NO: 5) and
LLSLALVGACITLGAYLGHK (SEQ ID NO: 6).

These and other peptides can be fused to carriers, for example, via peptide linkers. These linkers can range in size from about 2 amino acid residues to about 20 amino acid residues (e.g., from about 2 to about 16 amino acid residues, from about 2 to about 12 amino acid residues, from about 2 to about 9 amino acid residues, from about 2 to about 6 amino acid residues, from about 6 to about 20 amino acid residues, from about 9 to about 20 amino acid residues, from about 12 to about 20 amino acid residues, from about 6 to about 12 amino acid residues). The carriers can be, but are not limited to, a liposome, a nanoparticle, a cell penetrating peptide or a micelle. The peptide can also be linked to another peptide that targets a cell surface receptor in order to effect targeting of the peptide inhibitor to particular cell types. For example, the peptide can be linked to a ligand that binds to a cell surface receptor or an antibody that recognizes a cell surface protein.

In certain embodiments, the inhibition of Cyclophilin D is achieved by an antisense molecule. Antisense molecules can also be used to inhibit CyPD. For example,
5'-GTCCTCCCACTCTTAGAGCC-3' (SEQ ID NO: 7),
5'-GTCCTCCCACTCTTAGAGCC-3' (SEQ ID NO: 8),
5'-CTTCCCGCCTGTGCCATTGT-3' (SEQ ID NO: 9),
5'-GATGTCCTCCCACTCTTAGA-3' (SEQ ID NO: 10),
and
5'-TGTCCTCCCACTCTTAGAGCC-3' (SEQ ID NO: 11)
are examples of antisense molecules that can be used to inhibit CyPD.

In certain embodiments, the inhibition of Cyclophilin D is achieved by a siRNA molecule. Examples of siRNA molecules that can be used to inhibit CyPD include but are not limited to:

```
                                        (SEQ ID NO: 12)
5'-rGrGrArGrGrArCrArUrCrCrArArGrArArGrArUrUrGr

UrCAT-3'

(SEQ ID NO: 13)
5'-rArUrGrArCrArArUrCrUrUrCrUrUrGrGrArUrGrUrCr

CrUrCrCrCrA-3'

(SEQ ID NO: 14)
5'-rCrCrCrArArArGrArCrArGrCrUrGrArGrArArCrUrUr

CrAGA-3'
```

-continued

5'-rUrCrUrGrArArGrUrUrCrUrCrArGrCrUrGrUrCrUrUrUr
GrGrGrArC-3' (SEQ ID NO: 15)

5'-rGrCrUrCrCrArCrCrUrUrCrCrArCrArGrGrUrGrAr
UrCCC-3' (SEQ ID NO: 16)

5'-rGrGrGrArUrCrArCrCrCrUrGrUrGrGrArArGrGrUrGrGr
ArGrCrCrU-3' (SEQ ID NO: 17)

5'-rCrArGrArCrUrGrGrUrUrGrGrArUrGrGrCrArArGrCr
ArUGT-3' (SEQ ID NO: 18)

5'-rArCrArUrGrCrUrUrGrCrCrArUrCrCrArArCrCrArGrUrCr
UrGrUrC-3' (SEQ ID NO: 19)

5'-rGrGrCrUrArArUrGrCrUrGrGrUrCrCrUrArArCrArCrCr
AAC-3' (SEQ ID NO: 20)

5'-rGrUrUrGrGrUrGrUrArGrGrArCrCrArGrCrArUrUrArGr
CrCrArU-3' (SEQ ID NO: 21)

The CyPD inhibitors disclosed herein can be provided in a pharmaceutical composition. Depending on the intended route of administration, the pharmaceutical composition can be in the form of solid, semi-solid or liquid dosage forms (e.g., tablets, suppositories, pills, capsules, powders, liquids, or suspensions). The pharmaceutical composition can be preferably in unit dosage form suitable for single administration of a precise dosage. The unit dosage forms include a therapeutically effective amount of the agent described herein or derivatives thereof in combination with a pharmaceutically acceptable carrier and, in addition, may include other medicinal agents, pharmaceutical agents, carriers, or diluents. In the methods set forth herein, one or more CyPD inhibitors can be administered in combination or concomitantly with other therapeutic compounds that may be beneficial administered to the patient.

CyPD inhibitors may be administered via any suitable route of administration, for example, orally, intravenously, intramuscularly or subcutaneously. In certain preferred embodiments, the inhibitor of CyPD is administered orally. In certain preferred embodiments, the inhibitor of CyPD is administered intravenously, intramuscularly, or subcutaneously.

Suitable dosages may be devised based on a patient's particular needs. In general, dosages for CyPD inhibition, or enhancing cardiac function, or preventing or reducing the risk of or treating cardiomyopathy, decreased cardiac function, or decreased cardiac output, or a related disease or condition thereof in the newborn heart with CsA, NIM811 and Alisporivir may be in the range from about 0.5 mg/Kg to about 20 mg/Kg (e.g., from about 0.5 mg/Kg to about 5 mg/Kg, from about 1.0 mg/Kg to about 15 mg/Kg, from about 2.0 mg/Kg to about 15 mg/Kg, from about 5.0 mg/Kg to about 15 mg/Kg, from about 7.5 mg/Kg to about 12.5 mg/Kg, from about 1.0 mg/Kg to about 10 mg/Kg, from about 0.5 mg/Kg to about 10 mg/Kg, about 10 mg/Kg) PO or IV in humans.

In yet another aspect, the invention generally relates to a pharmaceutical composition comprising an inhibitor of CyPD or a pharmaceutically acceptable form thereof, in an amount effective in enhancing cardiac function, or preventing or reducing the risk of or treating cardiomyopathy, decreased cardiac function, or decreased cardiac output, or a related disease or condition thereof, in a neonate of a mammal, including a human, and a pharmaceutically acceptable carrier.

The pharmaceutical compositions of the invention may be used to treat any disease or condition where an enhanced cardiac function is deemed beneficial to the neonate, whether to treat, prevent or minimize the impact of such a disease or condition.

Pharmaceutical compositions of the invention may include any suitable CyPD inhibitors. In certain embodiments, the inhibitor of CyPD is selected from CsA, N-methyl-4-isoleucine cyclosporine, Alisporivir, GW5 and Sanglifehrin A.

In certain embodiments of the pharmaceutical composition, the inhibitor of CyPD is immunosuppressive (e.g., CsA). It is noted that for certain patients and/or diseases or conditions being treated, immunosuppressive agents may be preferably avoided. In certain preferred embodiment, the CyPD inhibitor is non-immunosuppressive (e.g., N-methyl-4-isoleucine cyclosporine, Alisporivir, GW5 and Sanglifehrin A).

In certain embodiments, the inhibitor of CyPD is N-methyl-4-isoleucine cyclosporine:

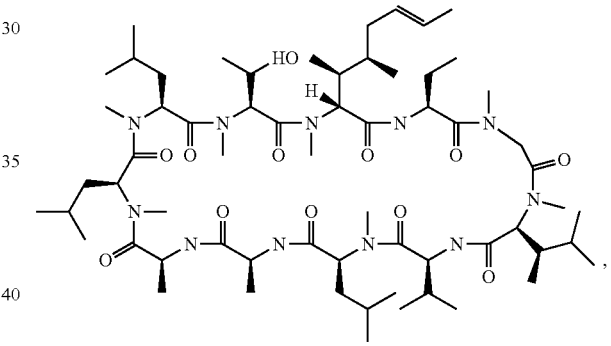

or a therapeutically active derivative thereof.

In certain embodiments, the inhibitor of CyPD is Alisporivir:

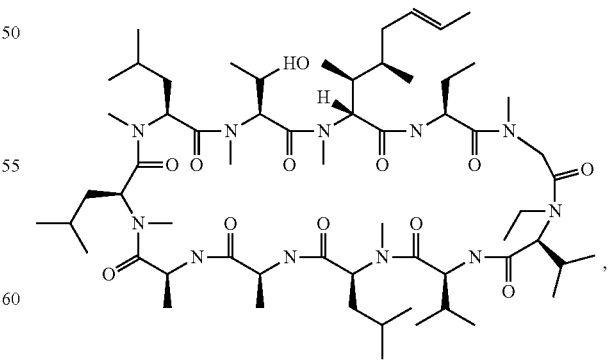

or a therapeutically active derivative thereof.

In certain embodiments, the inhibitor of CyPD is Sanglifehrin A:

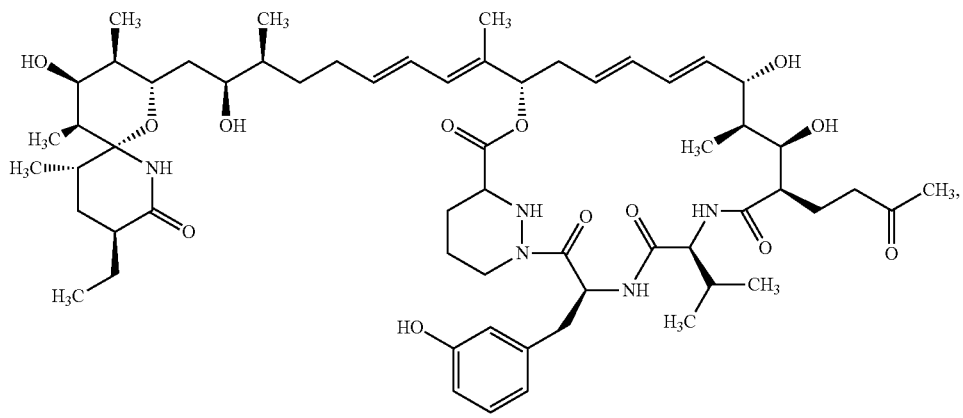 [SMILES: CC[C@H]1C[C@H](C)[C@@]2(NC1=O)O[C@@H](C[C@H](O)[C@@H](C)CC/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)c3)C(=O)N3CCCC(N3)C(=O)O1)[C@H](C)[C@H](O)[C@@H]2C]

or a therapeutically active derivative thereof.

In certain embodiments, the inhibitor of CyPD is GW5:

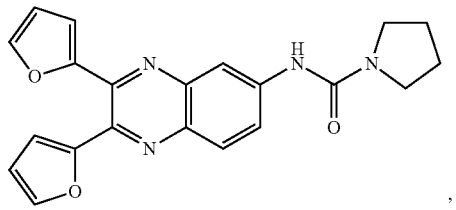 [SMILES: O=C(Nc1ccc2nc(-c3ccco3)c(-c3ccco3)nc2c1)N1CCCC1]

or a therapeutically active derivative thereof.

In certain embodiments, the inhibitor of CyPD is CsA:

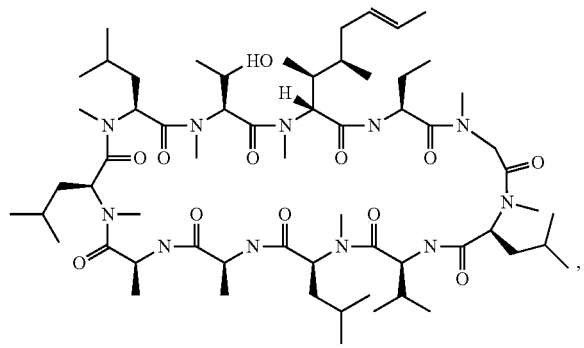 [SMILES: C/C=C/C[C@@H](C)[C@H](C)[C@@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@@H](C)C(=O)N(C)[C@@H](CC(C)C)C(=O)N(C)[C@@H](CC(C)C)C(=O)N(C)[C@@H](C(C)O)C(=O)N1C]

or a therapeutically active derivative thereof.

In certain embodiments, the inhibitor of CyPD is

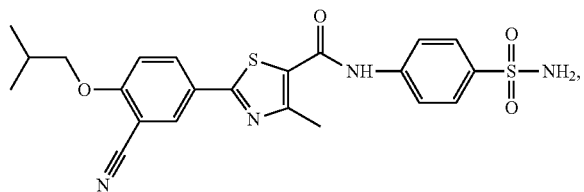 [SMILES: Cc1nc(-c2ccc(OCC(C)C)c(C#N)c2)sc1C(=O)Nc1ccc(S(N)(=O)=O)cc1]

or a therapeutically active derivative thereof.

In yet another aspect, the invention generally relates to a unit dosage form comprising a pharmaceutical composition disclosed herein.

In certain embodiments, the unit dosage is in the form of a tablet or capsule suitable for oral administration. In certain embodiments, the unit dosage is in the form of a liquid solution or suspension suitable for intravenous, intramuscular, or subcutaneous administration.

The following examples are meant to be illustrative of the practice of the invention, and not limiting in any way.

EXAMPLES

Supercomplex Assembly is Regulated by CyPD Activity

Studies have shown that opening the permeability transition pore decreases supercomplex assembly, while inhibition or deletion of CyPD increases supercomplex assembly in adult mice (FIG. 1), which suggest that CyPD's primary function is to regulate assembly of the ETC and that its activation of the mPTP may be a secondary effect of its role in ETC assembly. Inhibition of CyPD should secondarily close the mPTP and primarily increase the assembly of the ETC into supercomplexes. Recently published data (Etzler et al., 2017, Archives of Biochemistry and Biophysics, 613: 61-68) suggests that CyPD regulates supercomplex assembly, but, in contrast to data presented in FIG. 1, this report suggests that increased CyPD expression increases supercomplex assembly.

Adult heart mitochondria were used to show decreased supercomplex assembly after PTP opening and increased supercomplex assembly after PTP inhibition or deletion (FIG. 1). A: Mitochondrial permeability transition was induced by 60 µM free $Ca^{2+}$ (arrow) and was inhibited by 0.5 mM ADP or 200 nM CsA (top panel). Swelling, indicating PTP opening and a fall in absorbance, is reversible after the addition of 250 µM EGTA (arrow; bottom panel). B: Representative clear native immunoblot (upper) with corresponding densitometric analysis (lower) shows $Ca^{2+}$-induced PT decreases synthasome levels and that this is inhibited by 0.5 mM ADP and 200 nM CsA (n=7). The experimental conditions are summarized below the blot. Red bars indicate area scanned for analysis that is also presented above each blot, and denaturing immunoblots for VDAC below each blot demonstrated equal loading of samples (* $p \leq 0.05$, ** $p \leq 0.03$ by ANOVA). C: Immunoblotting (IB, for ATP5A) and ATP synthase in-gel assay (IGA) after CN electrophoresis demonstrated more synthasomes (red bars, areas replicated above each lane) in CypD KO hearts compared to WT hearts (upper panel) that was confirmed by densitometric quantification (lower panel). Note that the ATP synthase IGA results a white reaction product, so the shading is correct. (N=4, * p≤0.05, ** p≤0.001 by T-test).

In Vitro Testing of CsA and NIM811 on Primary Neonatal Cardiac Myocyte Cultures

In vitro experiments were carried out to study the effects of CsA and NIM811 on primary neonatal cardiac myocyte cultures. Hearts from wild type mice were used to test the effects of pharmacologic PTP closure with CsA and NIM811, and CyPD null hearts were used to test the effects of genetic PTP closure and the specificity of the drugs, which inhibit CyPD to close the PTP. Hearts were harvested in the first three days of life, and primary cultures of myocytes were treated daily for 5 days with Vehicle, 500 nM CsA, or 500 nM NIM811. In general, changes were observed in myocyte differentiation and mitochondrial structure and function when the PTP was closed using CsA and NIM811 or by deletion of CyPD, and CsA and NIM811 did not alter the effects of CyPD deletion.

PTP Closure with CsA, NIM811, or CyPD Deletion Increases Mitochondrial Structural Maturation In Vitro As mitochondria mature, the complexity of the mitochondrial network throughout the cell increases. Our in vitro data demonstrate that PTP closure increased mitochondrial length (aspect ratio) and mitochondrial network complexity (form factor) to levels that are generally associated with increased maturation of the mitochondrial network throughout the cell. (FIG. 2)

Wild type (WT) and CyPD null (−/−) neonatal ventricular myocytes were cultured for 5 days in the presence of vehicle (Veh), 500 nM CsA, or 500 nM NIM811, fixed, and stained with anti-OSCP antibody to label mitochondria. (a, b) Low (left, scale bar=20 μm) and high (right, scale bar=5 μm) magnification images of WT (a) and CyPD null (−/−) (b) samples demonstrate a mature mitochondrial morphology when the PTP was closed (treatment with CsA and NIM811, CyPD null) compared to control (Veh, WT). (c, d) Significant changes in aspect ratio (mitochondrial length) and form factor (network complexity) were associated with PTP closure. N=4-5 experiments and 45-90 mitochondria measured per condition; NS—not significant, *p<0.05, **p<0.01, †p<0.001, ‡p<0.0001 using Kruskal-Wallis with Dunn's multiple comparisons test to "Veh, WT". (FIG. 2)

PTP Closure with CsA, NIM811, or CyPD Deletion Increases Mitochondrial Membrane Potential In Vitro Increased mitochondrial maturation and activity is associated with an increase in mitochondrial membrane potential and a decrease in mitochondrial-derived oxidative stress (e.g., increased reactive oxygen species). Our in vitro data demonstrate that PTP closure increased mitochondrial membrane potential and decreased mitochondrial oxidative stress, two measures of increased mitochondrial function. (FIG. 3)

Neonatal cardiac myocytes from wild type (WT) or CyPD null (CyPD) mice were cultured in the presence of vehicle (Veh), 500 nM CsA, or 500 nM NIM811 for 5 days and stained for mitochondrial membrane potential ($\Delta\Psi m$, using tetramethylrhodamine, ethyl ester (TMRE)) and mitochondrial mass (MitoTracker Green (MTG)) and reactive oxygen species (ROS) levels (c, d) on day 6. (a) Merged fluorescence micrographs of mitochondria stained with TMRE/MTG; red/orange indicates high $\Delta\Psi m$ and green indicates low $\Delta\Psi m$. Scale bars=40 μm. (b) Statistical analysis revealed higher $\Delta\Psi m$ in WT myocytes treated with CsA or NIM811 and in CyPD null (−/−) myocytes, regardless of treatment. (c) Fluorescence micrographs of myocytes stained for ROS using 2'-7'-dichlorofluorescin diacetate. Scale bars=20 μm. (d) Statistical analysis revealed lower ROS levels in WT myocytes treated with either CsA or NIM811 and in CyPD null myocytes, regardless of treatment. N=3-5 experiments and 35-55 cells measured per condition; *p<0.05, **p<0.01, †p<0.001, ‡p<0.0001 using Kruskal-Wallis with Dunn's multiple comparisons test to "Veh, WT". (FIG. 3)

PTP Closure with CsA, NIM811, or CyPD Deletion Enhances Myocyte Differentiation In Vitro To examine levels of myocyte differentiation (FIGS. 4 and 5), specimens were co-labeled with antibodies α-actinin, which labels Z-bands, plus antibodies to cardiac troponin I (TNNI3, Tn-I) or T (TNNT2, Tn-T), which label myofibrils at the I-bands that flank the Z bands. Closing the PTP using genetic (CyPD null) or pharmacologic (CsA, NIM811) inhibition significantly increased myocyte differentiation but had no effect on cell proliferation or survival.

To validate the methods used, primary neonatal myocyte cultures from WT and CyPD null hearts were labeled with antibodies to α-actinin/troponin T or α-actinin/troponin I after 1, 3, or 5 days in culture. (a, b) Typical labeling with DAPI and antibodies to α-actinin/Tn-I (a) or α-actinin/Tn-T (b) at day 1, 3 and 5 in CyPD null (−/−) myocytes. Z-bands are labeled by anti-α-actinin and I-bands are labeled by anti-Tn-I and anti-Tn-T. The day 1 myocyte in (a) contains Z-banding pattern with anti-α-actinin but no I-banding pattern with anti-Tn-I; all other examples show clear Z- and I-bands. (c-e) Cultures were scored for the percent myocytes containing α-actinin (c), Tn-I (d) or Tn-T (e). In these untreated cultures, we found an increase in the number of cells labeled for both Z- and I-bands over the 5 days in culture. Compared to WT myocytes, CyPD null myocytes had slightly higher percentages of cells with Z- and I-bands at each age, and the percentage of cells with Z-bands was higher at each age than that for I-bands. N=2-4 experiments and 60-153 cells measured per condition. Scale bars=20 μm. (FIG. 4)

To determine the effects of PTP closure on myocyte differentiation, neonatal cardiac myocytes from wild type (WT) or CyPD null (CyPD) mice were cultured in the presence of vehicle (Veh), 500 nM CsA, or 500 nM NIM811 for 5 days, fixed, and stained for α-actinin and cardiac Troponin T (Tn-T) or Troponin I (Tn-I). (a, b) Merged fluorescence micrographs of WT (a) and CyPD null (−/−) (b) myocytes stained for α-actinin, DAPI and Tn-I or Tn-T demonstrate increased myocyte size and more organized myofibrils when the PTP is closed (WT with CsA or NIM811, all CyPD null). Scale bars=20 (c-d) Quantification of the percentage of myocytes positive for Z-bands (c, α-actinin) and I-bands (d, Tn-I) demonstrate that PTP closure increased myocyte differentiation. (e, f) When cultures were labeled with calcein-AM, Sytox orange, and Hoechst, there were no differences in live (e, Calcein/Hoechst) or dead (f, Sytox/Hoechst) cells between treatments. NS—not significant, *p<0.05, **p<0.01, ‡p<0.0001; N=4-5 experiments and 51-89 cells measured per condition and analyzed using ANOVA with Holm-Sidak's multiple comparisons test to "Veh, WT" (c, d) or 4-5 experiments with 2 replicates each measured per condition and analyzed using Friedman with Dunn's multiple comparisons test to "Veh, WT" (e, f). (FIG. 5)

Effects of PTP Closure Using CsA, NIM811, and CyPD Deletion on Cardiac Structure and Function In Vivo In vivo experiments were also carried out to study the effects of PTP closure on neonatal hearts in vivo. WT and CyPD null mice were treated daily from day 1 to day 5 of life with intraperitoneal injections of Vehicle (10% Solutol in phosphate buffered saline), 10 mg/kg CsA, or 10 mg/kg NIM811. Hearts were harvested and evaluated for wall thickness. In addition, in some cases, mice underwent echocardiography to measure left ventricular dimensions and function. Closure of the PTP significantly increased left ventricular ejection fraction, a measure of cardiac function.

CyPD Inhibition Increases LV Wall Thickness

WT and CyPD null (−/−) mice were treated with daily injections of vehicle (Veh) or CsA or NIM811 for 5 days, and hearts were harvested for hematoxylin and eosin staining one day after the last treatment. (a) Low power, short axis images of the left and right ventricles (LV, RV) demonstrate no changes in cardiac structure. Scale bar=1 mm. (b) There were no differences in total heart diameter (black bar in a-WT, Veh) between the groups. N=3-9 hearts measured per condition; NS—not significant using ANOVA with Dunnett's multiple comparisons test to "Veh, WT". (FIG. 6)

PTP Closure Increases Neonatal Cardiac Function

Mouse echocardiography was performed in the newborn period to measure cardiac function the day after the last injection of CsA and/or NIM811 (post-natal day (PND) 6) or when mice were weaned at about 3 weeks of age. These data demonstrate that PTP closure using CsA, NIM811, or deletion of CyPD increased cardiac function compared to WT animals that were not treated or treated with Vehicle in the neonatal period. These effects may be persistent, as most groups at weaning (except WT, vehicle and CsA treated) maintained higher ejection and shortening fractions. Also, at PND 6, the effects of CsA and NIM811 were specific to inhibition of CyPD as no additional or synergistic affects were seen with these drugs in CyPD null mice.

Wild type (WT) or CyPD null (CyPD) neonatal mice were not treated (No Tx) or treated with daily injections of vehicle (Veh, 10% Solutol in phosphate buffered saline), 10 mg/kg CsA, or 10 mg/kg NIM811 daily for 5 days (PND1-5). Mice were evaluated at PND6 or at weaning (Wean, PND21-24) for left ventricular ejection and shortening fraction, two measures of cardiac function, which was calculated using the left ventricular inner dimension in systole and diastole. Mice were anesthetized with 2-4% isoflurane and cardiac dimensions were made using M-mode echocardiography using a Vevo770 small animal ultrasound machine.

FIG. 7 demonstrates an example of echocardiogram data from neonatal mice treated for 5 days with Vehicle (Veh) or 10 mg/kg CsA. In each panel, the upper image is a 2-dimensional image showing the thorax and heart and the lower image is M mode of the LV. Bars mark the LV end diastolic (LVED) and systolic (LVES) dimensions, the IVS and LV posterior wall (LVPW). N=1 experiment. (FIG. 7)

FIG. 8 demonstrates that closure of the PTP in the first week of life increases cardiac ejection fraction and that this is sustained for up to three weeks of age in some treatment groups. WT and CyPD null (−/−) mice were not treated (No Tx) or treated with daily injections of vehicle (Veh) or CsA or NIM811 for 5 days. (a) Echocardiography performed at PND6 revealed increased EF (a) from 65% to 76-80% when the PTP was closed (WT+CsA or NIM811 or CyPD null). Treatment of CyPD null mice with CsA and NIM811 had no additional effect. (b) Echocardiography performed at PND6 (No Tx) compared to at weaning (as indicated in each column) revealed that the increased EF observed after closure of the PTP in (a) was sustained in WT mice treated with NIM811 and in CyPD null mice. N=5-25 mice evaluated per condition; NS—not significant, $*p<0.01$, $p<0.001$, $*p<0.0001$. (FIG. 8)

More experimental data can be found in Lingan J V, Alanzalon R E, Porter G A, Jr. 2017 "Preventing Permeability Transition Pore Opening Increases Mitochondrial Maturation, Myocyte Differentiation and Cardiac Function in the Neonatal Mouse Heart" *Pediatr Res*. In press. doi: 10.1038/pr.2017.19. PubMed PMID: 28141792, incorporated herein by reference in its entirety.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A method for enhancing cardiac function of a neonate of a mammal, comprising administering to the neonate an inhibitor of Cyclophilin D, or a pharmaceutically acceptable form thereof, in an amount effective to cause enhancement of the cardiac function of the neonate, wherein the neonate is from about 1 day to about 7 days old and has a secondary cardiomyopathy from the effects of open heart surgery.

2. The method of claim 1, wherein the inhibitor of Cyclophilin D is non-immunosuppressive.

3. The method of claim 1, wherein the inhibitor of Cyclophilin D is immunosuppressive.

4. The method of claim 1, wherein the inhibitor of Cyclophilin D is selected from Cyclosporine A, N-methyl-4-isoleucine cyclosporine, Alisporivir, 2,3-di(furan-2-yl)-6-(pyrrolidin-1-yl)carbonylamino quinoxaline (GW5) and Sanglifehrin A.

5. The method of claim 1, wherein the inhibitor of Cyclophilin D is administered orally.

6. The method of claim 1, wherein the inhibitor of Cyclophilin D is administered intravenously, intramuscularly, or subcutaneously.

7. A method for reducing the risk of or treating secondary cardiomyopathy from the effects of open heart surgery in a neonate of a mammal, comprising administering to the neonate thereof an inhibitor of Cyclophilin D, or a pharmaceutically acceptable form thereof, in an amount effective to cause enhancement of the cardiac function of the neonate, wherein the neonate is from about 1 day to about 7 days old undergoing open heart surgery.

8. The method of claim 7, wherein the inhibitor of Cyclophilin D is administered orally.

9. The method of claim 7, wherein the inhibitor of Cyclophilin D is administered intravenously, intramuscularly, or subcutaneously.

10. The method of claim 7, wherein the inhibitor of Cyclophilin D is non-immunosuppressive.

11. The method of claim 7, wherein the inhibitor of Cyclophilin D is immunosuppressive.

12. The method of claim 7, wherein the inhibitor of Cyclophilin D is selected from Cyclosporine A, N-methyl-4-isoleucine cyclosporine, Alisporivir, 2,3-di(furan-2-yl)-6-(pyrrolidin-1-yl)carbonylamino quinoxaline (GW5) or Sanglifehrin A.

13. The method of claim 7, wherein the inhibition of Cyclophilin D is achieved by an antisense molecule.

14. The method of claim 7, wherein the inhibition of Cyclophilin D is achieved by a siRNA molecule.

* * * * *